United States Patent [19]

Rigdon et al.

[11] Patent Number: 4,891,124
[45] Date of Patent: Jan. 2, 1990

[54] RFEFERENCE ELECTRODE FOR STRONG OXIDIZING ACID SOLUTIONS

[75] Inventors: Lester P. Rigdon, Livermore; Jackson E. Harrar, Castro Valley; Jack C. Bullock, Sr., Pleasanton; Raymond R. McGuire, Brentwood, all of Calif.

[73] Assignee: The United States of America as represented by The United States Department of Energy, Washington, D.C.

[21] Appl. No.: 355,523

[22] Filed: May 23, 1989

[51] Int. Cl.$^4$ ............................................. G01N 27/26
[52] U.S. Cl. .................................................... 204/435
[58] Field of Search ........................................ 204/435

[56] References Cited

U.S. PATENT DOCUMENTS 4,282,081  8/1981  Arrance, Sr. ....................... 204/435

Primary Examiner—John F. Niebling
Assistant Examiner—A. Phasge
Attorney, Agent, or Firm—Henry P. Sartorio; L. E. Carnahan; William R. Moser

[57] ABSTRACT

A reference electrode for the measurement of the oxidation-reduction potentials of solutions is especially suitable for oxidizing solutions such as highly concentrated and fuming nitric acids, the solutions of nitrogen oxides, $N_2O_4$ and $N_2O_5$, in nitric acids. The reference electrode is fabricated of entirely inert materials, has a half cell of Pt/Ce(IV)/Ce(III)/70 wt. % $HNO_3$, and includes a double-junction design with an intermediate solution of 70 wt. % $HNO_3$. The liquid junctions are made from Corning No. 7930 glass for low resistance and negligible solution leakage.

20 Claims, 3 Drawing Sheets

REFERENCE ELECTRODE FOR STRONG OXIDIZING ACID SOLUTIONS

The U.S. Government has rights to this invention pursuant to Contract No. W-7405-ENG-48 between the U.S. Department of Energy and the University of California, for the operation of Lawrence Livermore National Laboratory.

BACKGROUND OF THE INVENTION

In many industrial processes involving chemical solutions, the state of a chemical reaction may be measured by the potential (i.e., voltage) that develops between an inert electrode and a reference electrode immersed in the solution. This potential is known variously as the oxidation-reduction (ORP) or redox potential of the solution. In general, the potential that is measured reflects changes that are sensed by the inert electrode. The reference electrode ideally provides, as the name implies, a stable, constant reference point for the measured potential changes. In addition to stability and reproducibility of potential, practical applications of the ORP technique in industry require that both electrodes be mechanically rugged and resistant to corrosion by the process solutions.

Many devices have been designed and are commercially available for measuring ORP. These usually consist of an assembly consisting of both the inert, or indicating electrode, and a reference electrode. Indicating electrodes are almost always wires or disks of platinum or gold metal, or a less expensive substrate metal on which noble metals have been electroplated. Most reference electrodes embody half cells of the type metal/metal salt/solution, where the solution is in contact with the test solution whose redox potential is being measured. In this type of electrode, the salt is a sparingly soluble salt of the metal, and the solution contains anions of the salt. The most widely used examples of this type of electrode are the saturated calomel electrodes (SCE), with half cells having the composition $Hg/Hg_2Cl_2$/saturated KCl solution, and the silver/silver chloride electrodes, which is AgCl/solution saturated in AgCl and KCl (for example, U.S. Pat. Nos. 3,051,631 to Harbin and Munns, and 3,210,261 to Tyler). The reference electrode is usually fabricated so that its solution is in contact with the test solution at a porous junction. This junction, typically made of porous ceramic (for example U.S. Pat. Nos. 4,495,052 to Brezinski, and 4,495,053 to Souza) or plastic, fritted glass, or a small orifice, is selected to prevent excessive loss of the reference electrode solution, and mixing of it with the test solution, while maintaining a reasonably low electrical resistance for the potential measurement.

Most chemical processes and laboratory experiments requiring the measurement of ORP can employ reference electrodes found in the prior art, and which are commercially available. However, new chemical processes are being developed which involve the use of highly-concentrated, fuming nitric acids containing very strong oxidizing agents such as dinitrogen tetroxide, $N_2O_4$, and dinitrogen pentoxide, $N_2O_5$. These solutions include 100% $HNO_3$, red fuming nitric acid, which is 20–40 wt. % $N_2O_4$ in $HNO_3$, and mixtures of $HNO_3$, $N_2O_4$, and $N_2O_5$. Conventional reference electrodes are unsuitable for measurements of these solutions for several reasons. First, these nitric acid media are extremely aggressive toward the mechanical components of the electrode. Only glass, gold, the platinum metals, certain refractory metals such as tantalum, and certain fluorocarbon plastic materials are inert. Secondly, nitric acid media are especially reactive toward the half-cell metals, mercury and silver, of the conventional reference electrodes. Third, strong nitric acid and the nitrogen oxides react with chloride to form chlorine, which is detrimental to the functions of the reference electrode. Reference electrodes based on mercurous sulfate or oxide can be used to eliminate this problem, but the reactivity of mercury remains.

A type of reference electrode more suitable for use with strong nitric acid media is the redox type, which consists of an inert metal in contact with a solution containing the oxidized and reduced forms of an oxidation-reduction system. Examples of this type of electrode that have been used are gold with the Fe(III)/Fe(II) couple and platinum with iodine/iodide (U.S. Pat. No. 4,495,050, Ross). With equimolar concentrations of the oxidized and reduced forms of the couple, the potential of this reference electrode is established and buffered, or "poised" electrochemically, at a value corresponding to the formal potential of the couple in the electrode solution.

For compatibility with strong nitric acid media, the redox-type reference electrode should be based on solutions of nitric acid, and the redox couple chosen should be one whose formal potential is close to the potentials of the solutions to be measured. The redox couples used in the prior art, such as Fe(III)/Fe(II) and $I_2/I^-$ mentioned above, would be unstable in potential because the reduced species, Fe(II) and $I^-$, would react rapidly with the nitric acid media.

SUMMARY OF THE INVENTION

Accordingly, it is an object of the invention to provide a reference electrode for strong oxidizing acid solutions.

It is also an object of the invention to provide a redox type reference electrode for use with strong nitric acid media.

The invention is a stable, unreactive, and corrosion-resistant reference electrode for application to ORP measurement in highly oxidizing solutions such as strong, fuming nitric acids containing nitrogen oxides. The invention comprises a double-junction assembly, with a half cell comprising a platinum wire or rod immersed in an equimolar solution of cerium(IV) and cerium(III) in 70% nitric acid, and an intermediate junction of 70% nitric acid. The Ce(IV)/Ce(III)/70% $HNO_3$ half cell has a formal potential of +1.15 V vs. the saturated calomel electrode. The reference electrode junctions are made from Corning No. 7930 porous glass, and the body and fitting components of the electrode are made of Kel-F and PTFE Teflon. The electrode could be used for other purposes, such as alloy corrosion potential measurement, where a stable reference is required for electrochemical measurements.

DETAILED DESCRIPTION OF THE INVENTION

Figure 1:
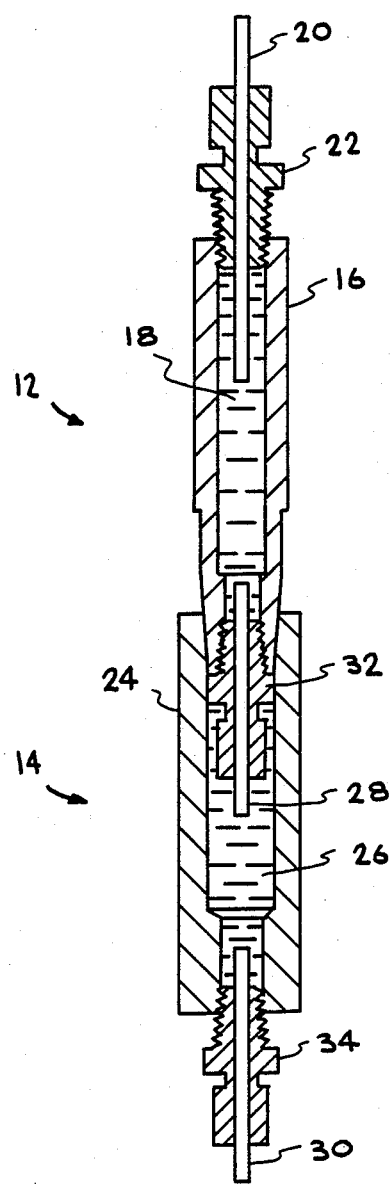
FIG. 1 is a sectional view of a double-junction reference electrode according to the invention.

A preferred double junction embodiment of the invention is illustrated in FIG. 1. The electrode 10 has two compartments: the reference half cell 12 and the liquid-junction compartment 14. Half-cell 12 is made of a half-cell body 16 which contains an equimolar solution 18 of Ce(IV)/Ce(III) in 70% $HNO_3$. A platinum electrode (rod or wire) 20 extends into solution 18 through Swagelok fitting 22 which is fitted into one end of cell body 16. Liquid junction compartment 14 is made of compartment body 24 which contains a solution 26 of 70% $HNO_3$ and which is connected to half-cell body 16. The connection between the half-cell 12 and the liquid-junction compartment 14, and the connection from the latter to the process solution is made via solution-soaked porous-glass junctions 28, 30 respectively. These are fabricated by machining oversize rods of Corning No. 7930 glass to a diameter of 0.125 in. to fit into suitable tube fittings, e.g. standard Swagelok fittings 32, 34 respectively. The inner hole of the body of the Swagelok fitting is drilled through to 0.128 in. so that the 0.125-in. rod can easily slide through the hole. Prior to use in the reference electrode, the glass is cleaned by soaking overnight in two portions of N,N-dimethyl formamide, followed by several days soaking in water. To facilitate reaching a low resistance when put into use, the porous glass rods are kept under water until fitted into the reference-electrode assembly. Corning No. 7930 glass, which is 96% silica, is known to be a reliable material where chemical resistance, low solution flow, and low junction electrical resistance are desired.

The solution of the reference half-cell is 0.05 Mol/L in Ce(IV) and Ce(III). It is prepared by dissolving 27.41 g of $(NH_4)_2Ce(NO_3)_6$ and 21.71 g of $Ce(NO_3)_3 \cdot 6H_2O$ in about 900 mL of reagent-grade, 70 wt. % $HNO_3$, then diluting to 1 L with the $HNO_3$. The half-cell solution can be replaced easily by removing the platinum rod, aspirating the old solution, and then refilling. The solution in the liquid-junction compartment can likewise be replaced by removing the porous-glass rod. The entire assembly can be disassembled for service or glass rod replacement, and reassembled in a few minutes. The platinum electrode is cleaned initially by boiling in concentrated HCl, followed by boiling in reagent-grade, 70 wt. % $HNO_3$.

More generally, the invention comprises a Metal/Ce(IV)/Ce(III)/Solution half-cell where the metal is preferably platinum, but may also be gold, another platinum metal such as rhodium or iridium, or platinum plated on a conductive surface, and the solution is preferably 70 wt. % $HNO_3$, but may be another mineral acid such as $H_2SO_4$. The half-cell may be used by itself, or preferably in a double junction design with an intermediate junction filled with the same or other solution. The cell bodies are made of materials such as Kel-F and PTFE Teflon. The junction between the two cell compartments and to the test solution is preferably a porous glass, but may also be a porous ceramic such as alumina or zirconia or other porous material such as porous plastic. Tube fittings may be used or the porous material may be force fit into the cell body.

The reference electrode is designed to be inserted into a tube-type fitting in the process piping. Depending on the size of the fitting, either end of the assembly can be fitted with the platinum electrode, rather than the smaller diameter end as shown in FIG. 1. Threading of the body of the reference electrode would permit a pipe-thread connection.

As shown in FIG. 1, the liquid-junction compartment of the reference electrode is filled with reagent-grade, 70 wt. % $HNO_3$. This compartment provides an intermediate solution junction that is compatible with the solutions of both the half-cell and the strong nitric acid process solutions. Depending on the process solutions being measured, other solutions could be substituted. The half-cell might be connected through a single junction to the process solutions, with satisfactory performance for short periods of time, but for longer-term reliability, and especially since the process solutions are usually at a higher pressure than the internal solutions of the reference electrode, this electrode was primarily designed with the double-junction configuration. However, the invention includes the half-cell by itself. Rather than using the Swagelok fitting, the intermediate porous rod in the assembly can also be installed by force fitting into a hole drilled in the bottom of the half-cell compartment.

After complete assembly of the reference electrode with the internal solutions, the tip is immersed in 70 wt. % $HNO_3$, and it is stored in this solution when not in use. After at least 24 hours to allow equilibration of the solutions in the junctions, the potential of the electrode is measured against that of a saturated-calomel (SCE) or Ag-AgCl electrode. If known to be reliable, this check electrode can be the half-cell of a commercial pH electrode; otherwise an SCE can be prepared according to standard electrochemical procedures. To measure the potential, either a pH meter in the "absolute" emf or mV mode, or digital voltmeter, is used, and both the reference electrode and the check reference electrode are immersed in a saturated solution of KCl. The measured potential within a few seconds should be $+1.15\pm0.01$ V vs. SCE or $+1.20\pm0.01$ V vs. Ag-AgCl. Erratic or improper readings are probably due to contaminated or unequilibrated porous-glass junctions. The Ce(IV)/Ce(III) reference electrode should not be left in the KCl solution for more than a minute or two.

All of the materials of construction of the reference electrode—Kel-F, PTFE Teflon, glass, and platinum—are indefinitely resistant to attack by the fuming nitric acids and nitrogen oxides.

Figure 2:
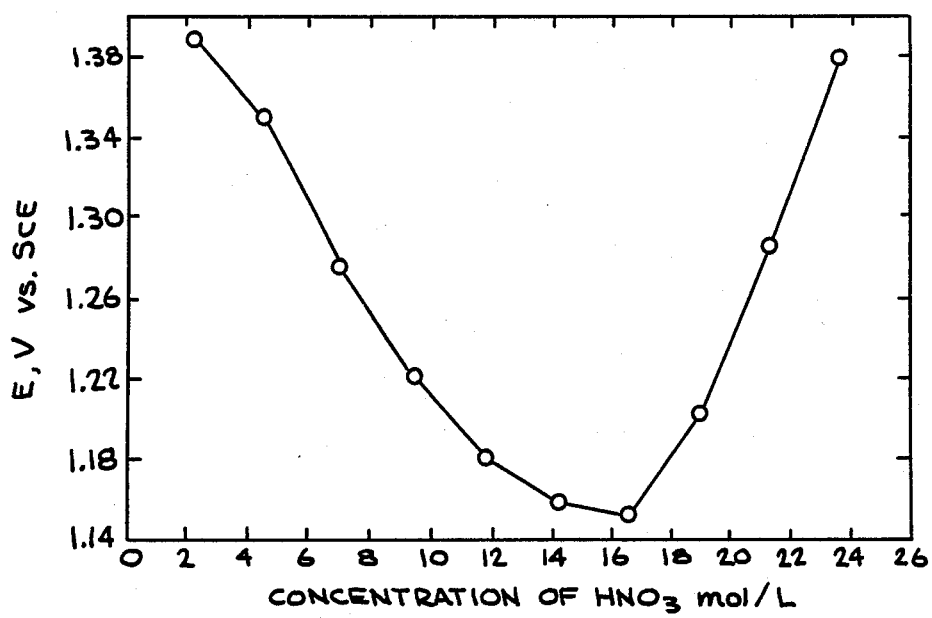
FIG. 2 is a graph of the potential of the Pt/Ce(IV)/Ce(III)/$HNO_3$ half cell, measured in volts vs. SCE, as a function of $HNO_3$ concentration.

To characterize the Ce(IV)/Ce(III) half-cell system selected for use in the reference electrode, the redox potential of the couple was measured as a function of nitric acid concentration, with the results shown in FIG. 2. As can be seen, there is fairly broad minimum in the potential in the vicinity of 16 Mol/L $HNO_3$, which is the concentration of reagent-grade, 70 wt. % nitric acid. Since this composition corresponds to the point of least sensitivity of the potential to changes in composition, and is a convenient one to obtain, this solution was chosen as both the half-cell medium, and as the intermediate solution for the double-junction reference electrode. This solution also is expected to minimize the magnitude of the liquid junction potentials involved in the measurements of the strong nitric acid solutions.

Although modern voltage-measuring equipment is of high input impedance and can tolerate rather high source resistances in sensors such as pH and ORP apparatus, a reasonably low resistance is desirable so that noise pickup and loss of signal is minimal. Essentially all of the resistance of the disclosed reference electrode is found in the porous glass junctions. The ac electrical resistance of each of these junctions in 90 wt. % $HNO_3$ is 690 ohms. The resistances of these junctions would be of this order of magnitude for all of the range of strong nitric acids and nitric acid solutions of nitrogen oxides.

To test the stability of the reference electrode and demonstrate its use in the measurement of the ORP of process solutions, the reference electrode was installed together with a platinum indicator electrode in a 1-inch Teflon pipe tee. The pipe tee was filled with solution for the static stability tests, and solution was flowed through it for the process solution measurements.

Figure 3:
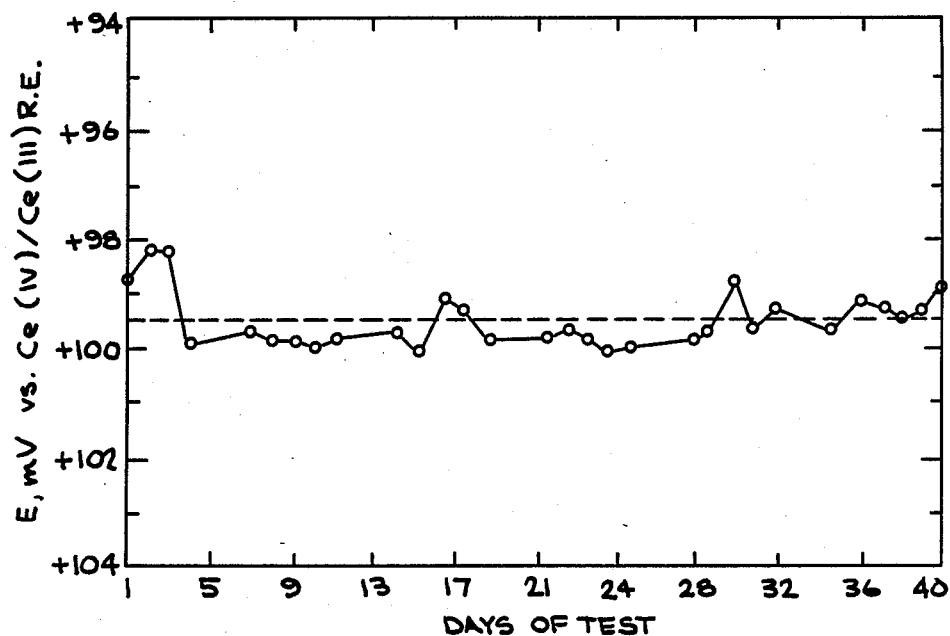
FIG. 3 is a graph illustrating the stability of potential of the Ce(IV)/Ce(III) reference electrode (R.E.) in measuring ORP with a Pt indicator electrode.

Good stability of the potential of the reference electrode for reasonable periods of time, under the diverse conditions of use, is one of the prerequisites of accurate, reproducible redox potential measurement. The stability of the reference electrode was evaluated under the ambient laboratory conditions in two tests, and in a third test under controlled-temperature conditions. Because a second electrode is required for a redox potential measurement, the tests actually measure more than just the stability of the reference electrode; nevertheless, the tests are a valid indication of the performance of the individual components, as well as the overall measurement assembly. In one test, the results of which are shown in FIG. 3, the redox potential (E) of a solution of Ce(IV) and Ce(III) in $H_2SO_4$ was measured with a platinum electrode and the Ce(IV)/Ce(III)/$HNO_3$ reference-electrode assembly. In this test, the temperature of the laboratory varied between 20° and 25° C. (68° and 77° F.), and as can seen in FIG. 3, the potential variation was within the range of about 2 mV, which is excellent stability.

In a second test, the redox potential of red-fuming nitric acid (RFNA) solution was measured in the Teflon pipe tee, with a 14-psi pressure applied to the RFNA solution by means of nitrogen gas. RFNA is 18 wt. % $N_2O_4$, 1.6 wt. % $H_2O$, and the balance $HNO_3$. The pressure test was designed to examine the possible effect of process solution pressure on both the mechanical integrity of the measuring assembly, and the possible effect of the diffusion of the constituents of the RFNA on the potential of the reference electrode assembly. During the pressure test, which lasted for 40 days, the ambient temperature varied from 16° to 23° C. (61° to 73° F.). There was no evident external or internal leakage of the assembly. The measured potential fluctuated slowly up and down, apparently with the temperature, with the extreme variations being within a range of 9 mV. There was no long-term offset or indication of deterioration of the measurement, thus this is certainly fairly good stability for the device. If more extreme temperature variations are encountered on a plant floor, further tests may be required to measure the temperature coefficient more exactly.

The third test of the redox-potential measuring assembly was performed by placing it in a temperature-controlled chamber. The temperature of the chamber cycled between 22° and 26° C. in short intervals, but the lag time of the test assembly moderated the electrode and test solutions to about a 1° C. variation. The pressure on the reference electrode was maintained at 13.5±0.2 psi for four days, and then reduced to ambient pressure for another four days. The measured potential slowly drifted from 68 to 72 mV during the four days at 13.5 psi pressure. It drifted from 72 to 73 mV during the subsequent four days at ambient pressure. The potential of the reference electrode was 1.149 V vs. SCE following the 48 days of the second and third series of tests described.

The reference electrode was further tested by using it in the measurement of solutions produced in an electrolysis process. In this electrolysis process, $N_2O_4$ in nitric acid is oxidized anodically to produce solutions of $N_2O_5$. The ORP of the solution was monitored by pumping the solution in a recycle loop between the electrolysis cell and the redox-potential measuring assembly while the electrolysis was in progress. The measured ORP values were recorded for complete electrolyses in which all of the $N_2O_4$ is transformed to $N_2O_5$. The concentrations of the constituents in the solutions were measured and they have been correlated with ORP.

EXAMPLE 1

Figure 4:
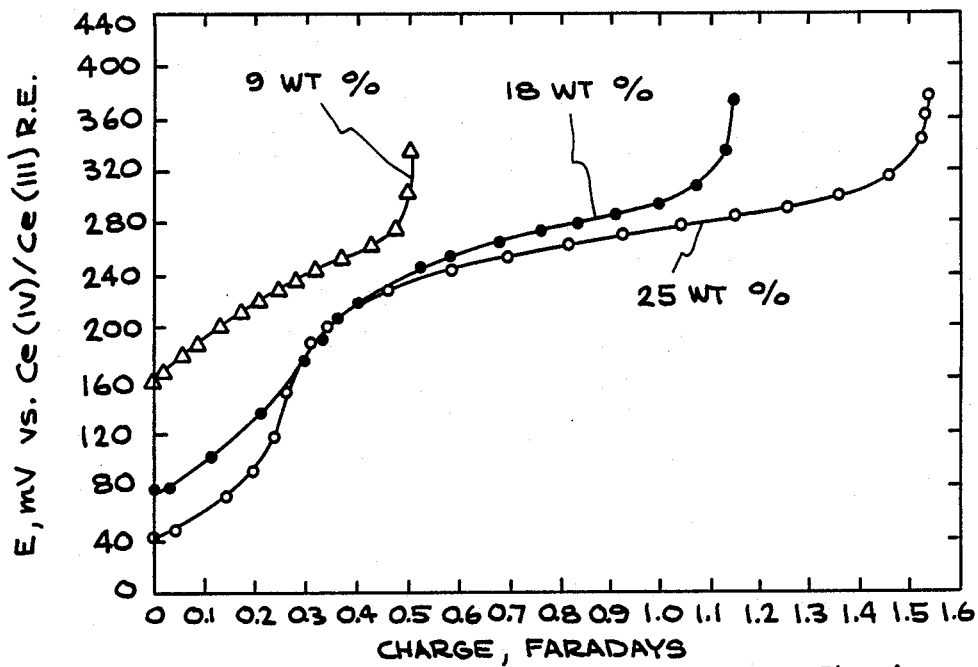
FIG. 4 is a graph of ORP of analyte solutions during electrosynthesis of $N_2O_5$ in $HNO_3$ by oxidation of $N_2O_4$, for three initial concentrations of $N_2O_4$ (9, 18, 25 wt. %)

Measurement of Redox Potential of Anolyte During Electrolysis of Three Different Solutions of $N_2O_4$ ORP curves for three initial concentrations of $N_2O_4$ (9, 18, and 25 wt. %) are shown in FIG. 4. The ORP becomes more positive as the electrolysis proceeds because the solution becomes more oxidizing in character. Qualitatively, the shapes of these curves can be explained as follows. The first potential excursion, which can be seen clearly on the 18 and 25 wt. % $N_2O_4$ curves in the charge (quantity of electricity) range of 0.2-0.4, is due to the consumption of water in the acid by the electrogenerated $N_2O_5$. When water is present, $N_2O_5$ reacts with it to form $HNO_3$. The ORP rapidly becomes more positive when all of the water has been used up. The solution potential is then determined by the ratio of the concentrations of $N_2O_5$ and $N_2O_4$, and it increases slowly as the electrolysis continues. At the end of the electrolysis, when all of the $N_2O_4$ has been used up, there is a very rapid shift in the ORP to more positive values. The solution at this point is a solution of $N_2O_5$ in $HNO_3$. By suitable calibration of the ORP apparatus and measurement of other parameters of the solution, the concentrations of the constituents in the solutions can be determined.

EXAMPLE 2

Figure 5:
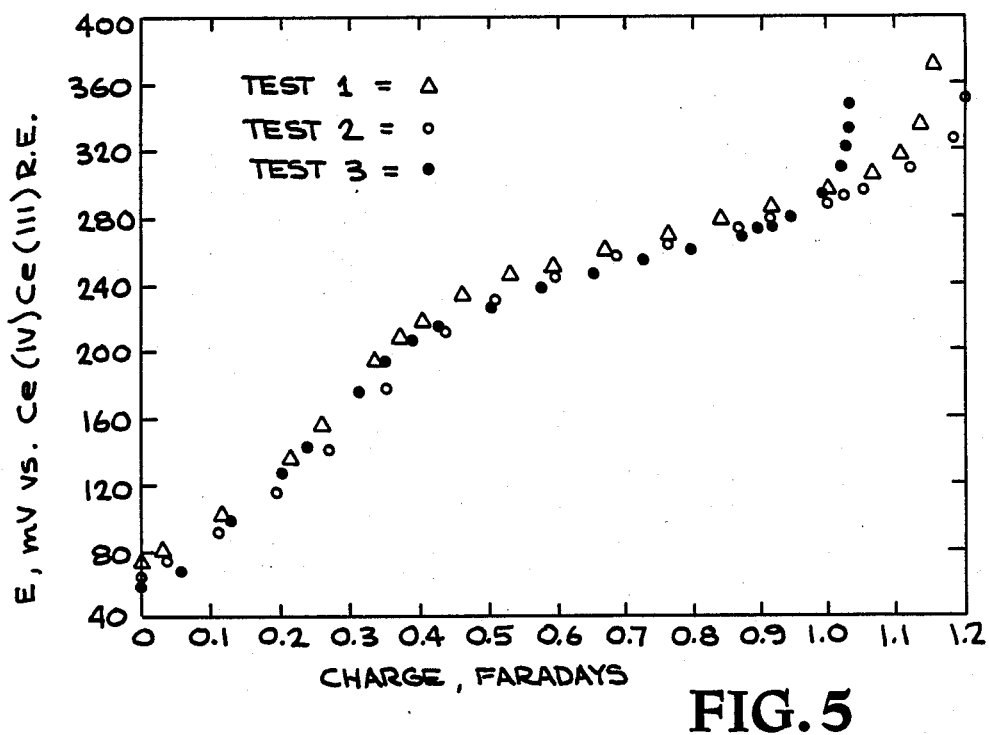
FIG. 5 is a graph of ORP during electrolysis of three 18 wt. % $N_2O_4$ solutions at approximately one-month intervals.

Measurement of Redox Potential of Anolytes During Electrolysis of Three Different Solutions at One Month Intervals FIG. 5 shows the results of measurement of the ORP during electrolysis of three 18 wt. % $N_2O_4$ solutions at approximately one-month intervals. This illustrates the good reproducibility of the measurement using the reference electrode. The final ORP excursion for these solutions is slightly different because the quantities of solution were different.

Changes and modifications in the specifically described embodiments can be carried out without departing from the scope of the invention which is intended to be limited only by the scope of the appended claims.

We claim:

1. A reference electrode suitable for long-term, reproducible measurement of the oxidation-reduction potential (ORP) of strong oxidizing acid solutions, comprising a half cell of Metal/Ce(IV)/Ce(III)/Mineral Acid Solution.

2. The apparatus of claim 1 wherein the half cell is a half cell of Pt/Ce(IV)/Ce(III)/70 wt. % $HNO_3$ which has a formal potential of +1.15 V vs. a saturated calomel electrode.

3. The apparatus of claim 1 wherein the Metal is selected from platinum, gold, rhodium, iridium, or platinum plated on a conductive substrate.

4. The apparatus of claim 1 wherein the Mineral Acid Solution is selected from $HNO_3$ and $H_2SO_4$.

5. The apparatus of claim 1 further comprising an intermediate junction connected to the half cell.

6. The apparatus of claim 5 wherein the intermediate junction is a solution of $HNO_3$ or $H_2SO_4$.

7. The apparatus of claim 2 further comprising an intermediate junction of 70 wt. % $HNO_3$ connected to the half cell.

8. The apparatus of claim 1 further comprising a liquid junction of porous glass, porous ceramic or porous plastic extending from the half cell.

9. The apparatus of claim 8 further comprising mounting means in the half cell for attaching the liquid junction to the half cell.

10. The apparatus of claim 8 wherein the liquid junction is formed of Corning No. 7930 glass.

11. The apparatus of claim 8 wherein the liquid junction is formed of alumina or zirconia.

12. The apparatus of claim 5 further comprising a first liquid junction of porous glass, porous ceramic or porous plastic extending between the half cell and the intermediate junction and a second liquid junction of porous glass, porous ceramic or porous plastic extending from the intermediate junction.

13. The apparatus of claim 12 wherein the liquid junctions are Corning No. 7930 glass.

14. A reference electrode suitable for long-term, reproducible measurement of the oxidation-reduction potential (ORP) of solutions of highly-concentrated (fuming) nitric acids and nitric acids containing the highly oxidizing nitrogen oxides, $N_2O_4$ and $N_2O_5$, comprising:
   a half cell body;
   a half cell solution of Ce(IV)/Ce(III)/70 wt. % $HNO_3$ in the half cell body;
   a platinum electrode extending into the half cell body; and
   a first liquid junction extending from the half cell body.

15. The apparatus of claim 14 further comprising:
   an intermediate junction cell body connected to the half cell body with the first liquid junction extending therebetween;
   an intermediate junction solution of 70 wt. % $HNO_3$ in the intermediate cell body; and
   a second liquid junction extending from the intermediate junction cell body.

16. The apparatus of claim 14 wherein the first liquid junction is formed of porous glass, porous ceramic or porous plastic.

17. The apparatus of claim 15 wherein the first and second liquid junctions are formed of porous glass, porous ceramic or porous plastic.

18. The apparatus of claim 16 wherein the first liquid junction is formed of Corning No. 7930 glass.

19. The apparatus of claim 17 wherein the first and second liquid junctions are formed of Corning No. 7930 glass.

20. The apparatus of claim 15 further comprising tube fittings mounted in the cell bodies for holding the platinum electrode and the first and second liquid junctions.

* * * * *